United States Patent [19]

Ladd

[11] 4,132,230
[45] Jan. 2, 1979

[54] RESTRAINING GARMENT

[76] Inventor: James T. Ladd, 500 S. Broadway, Portland, Tenn. 37148

[21] Appl. No.: 827,188

[22] Filed: Aug. 23, 1977

[51] Int. Cl.² ............................................. A61F 13/00
[52] U.S. Cl. ................................................... 128/134
[58] Field of Search ................................ 128/133–135; 5/336

[56] References Cited

U.S. PATENT DOCUMENTS

| | | | |
|---|---|---|---|
| 2,664,083 | 12/1953 | Heymans | 128/134 |
| 2,851,033 | 9/1958 | Posey | 128/134 |
| 3,437,089 | 4/1969 | Posey | 128/134 |
| 3,466,090 | 10/1969 | Posey | 128/134 |
| 3,565,483 | 10/1971 | Posey | 128/134 |
| 3,612,605 | 12/1971 | Posey | 128/134 |
| 3,641,997 | 4/1972 | Posey | 128/134 |
| 3,669,107 | 6/1972 | Posey | 128/134 |
| 3,788,309 | 1/1974 | Zeilman | 128/134 |
| 3,901,229 | 8/1975 | Hensel | 128/134 |
| 4,026,282 | 5/1977 | Thomas | 128/134 |

*Primary Examiner*—Lawrence W. Trapp
*Attorney, Agent, or Firm*—C. Claborne Carter

[57] ABSTRACT

A pull-over restraining garment for comfortably and securely confining a subject to a bed, chair or other supporting structure comprising a vest member disposed about the upper torso and secured to the subject by means of a detachable coupling crotch strap and an elongated strap member which is detachably coupled to the frame of the bed, chair or other supporting structure to which the subject is confined. The elongated strap and vest are slidably interconnected by means of an elongated strap being slidably received by a large loop formed at the rear of the vest by a first transverse strap, disposed about the thorax of the subject, which is integrally attached to the front of the vest and free at the rear. The patient is held to the approximate center of the bed, chair or other supporting structure by means of a smaller second loop with ends spatially disposed from the ends of the elongated strap and fixedly attached to said elongated strap in the center of its underside, slidably receiving the first loop and thereby limiting the travel of the first loop, formed at the rear of the vest, on the elongated strap. A second transverse strap on the vest is disposed about the waist of the subject, at the bottom hem of the vest, and has fixedly connected at its midpoint at the rear of the vest, the crotch strap which extends through the thighs of the subject and detachably couples to the vest at its front midpoint on the second transverse strap.

3 Claims, 5 Drawing Figures

RESTRAINING GARMENT

BACKGROUND OF THE INVENTION

1. Field of the Invention

This invention relates to restraining devices and more particularly to an improved garment for comfortably and securely confining persons to supporting structures or the like.

2. State of the Prior Art

Belts, harnesses and shoulder straps of various forms are frequently used in applications where persons must be confined because of infirmity, invalidity or other protective purposes. Such devices are well known to practitioners of the healing arts and others who utilize such devices in hospitals, sanatoriums, convalescent homes and similar applications where it is necessary to assist a person who is incapable of fully controlling his or her movements. Exemplary of some of the prior art devices are the following U.S. Pat. Nos.: 2,851,033; 3,437,089; 3,466,090; 3,565,483; 3,612,605; 3,641,997; 3,669,107; and 3,901,229.

Many of these devices, however, are unsatisfactory because of aesthetic appearance; inconvenience due to weight, size or ease in application or release; comfort or acceptance by the patient; and inadequate security of the device; Additionally, the attendant frequently had to chose the type of restraining device to be used based more upon application rather and patient comfort.

SUMMARY OF THE INVENTION

Accordingly, the deficiencies of the prior art devices are obviated by the present invention which provides a strong and durable, lightweight device, simple in construction and of relatively low cost, that is easily and quickly released in the event of emergency. A person wearing the present invention will be comfortably confined, and yet unable to escape or fall from his or her bed, wheel chair or other supporting structure without the assistance of an attendant. When applied, the present invention allows reasonable freedom of movement so that the person restrained has an acceptable degree of personal comfort and relaxation regardless of his or her idiosyncrasies. Additionally, skin irritations and other discomforts normally caused by tightly fitting belts, harnesses and shoulder straps are avoided even after extended periods of use.

The present invention cannot be slipped out of by the patient as can other prior art devices, is made of soft and flexible materials, and can be laundered by ordinary methods, requiring no special care. Briefly, it includes a vest member, made of any lightweight material such as cotton, synthetic fiber, synthetic mesh, or the like; and a multiplicity of straps made of a soft material, webbing or the like, either fixedly attached or detachably coupled to the vest by means of snaps, buckles, clasps, velcro strips or simple knots. While the number of detachable coupling means could be increased to make the present invention adjustable, the preferred form is not adjustable and must be selected by the attendant based upon the age, size, and weight of the subject. This selection assures a better fit and improves security.

In use, the vest member is disposed around the upper torso of the subject to make a comfortable fit and aesthetic appearance. The first transverse strap of the vest extends about the thorax of the subject, giving support to him or her and reinforcement to the vest, and is integrally attached to the front portion of the vest while forming a large first loop at the rear of the vest. The second transverse strap of the vest extends about the waist of the subject, giving him or her added support, affording reinforcement for the vest, and creating additional effectiveness for security by means of having the crotch strap attached to it, thereby rendering the vest member virtually escape proof. However, the present invention can be escaped from in the event of an emergency by cutting in half the large first loop formed at the rear of the vest by the first transverse strap.

In use, the elongated strap member is slidably received by the large first loop formed at the rear of the vest member by the first transverse strap and freely travels therethrough except as limited by the smaller second loop located on the underside of the elongated strap and integrally fixed thereto with its ends being spatially disposed from the ends of the elongated strap for the purpose of restraining the subject to the approximate center of the bed, chair or other supporting structure. This limitation in movement by the subject is accomplished by the smaller second loop slidably receiving therethrough the larger first loop formed at the rear of the vest member by the first transverse strap.

The present invention can be easily applied on the wearer by the wearer or by an attendant since the vest has a pullover design. Sleeves may be utilized on the vest, but their use does reduce the ease in application. With or without sleeves, the present invention has the appearance of an ordinary garment and not that of the usual restraining devices. Therefore, approval and cooperation of the subject wearing the present invention is much greater than with other currently available devices. Additionally, no other restraining device is currently known which is so readily adaptable from bed to chair to other supporting structures. The interaction of the elongated strap member and the large first loop formed at the rear of the vest member essentially restrains forward movement of the subject while the interaction of the small second loop located on the underside of the elongated strap member and the large first loop restrains lateral movement of the subject. Most of the prior art devices were successful in only limiting movement in either the forward or lateral direction and could not accomplish both without a considerable loss in comfort.

BRIEF DESCRIPTION OF THE DRAWINGS

These and other aspects of the invention will be more fully understood from the following detailed description and an explanation of the accompanying drawings in which.

DETAILED DESCRIPTION

Throughout the description that follows, like numerals refer to similar parts in the various drawings.

Figure 1:
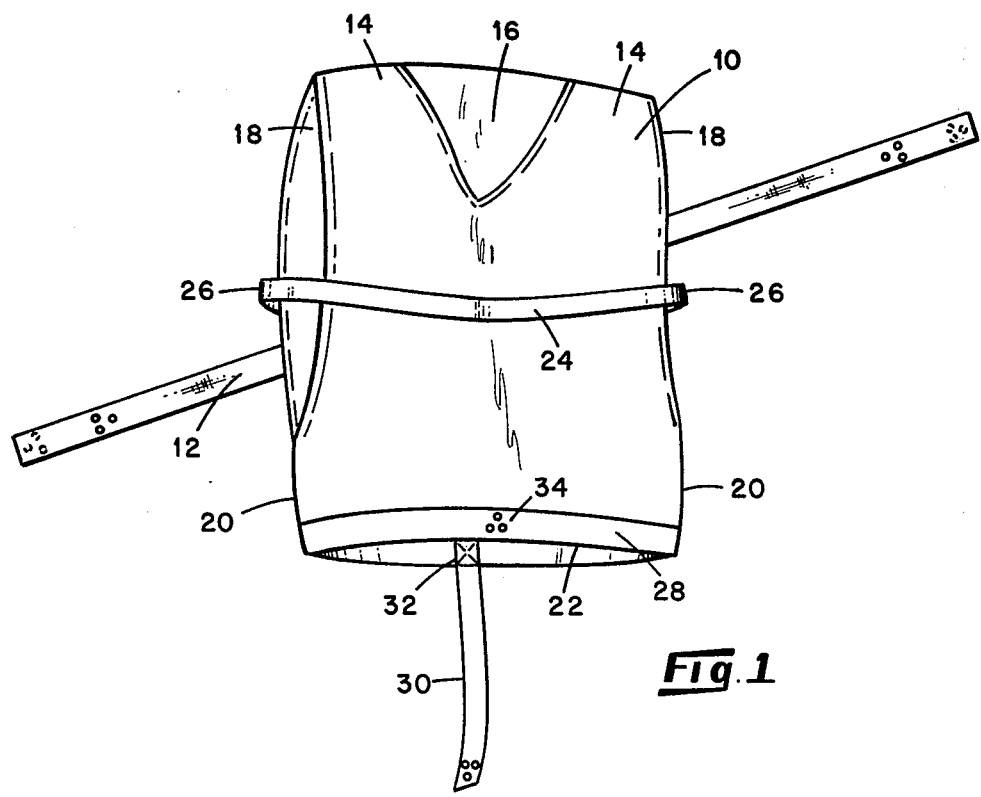
FIG. 1 is a perspective view showing the preferred form of the restraining garment.

Referring to the drawings and particularly to FIG. 1, the preferred form of the restraining garment comprises a jacket member 10 and an elongated strap member 12 which is secured to the jacket 10 by means more fully hereinafter described.

The jacket 10 may be made of a single piece of suitable clothlike material folded at its middle to form a shoulder section 14 after an opening 16 has been therefrom cut for receiving the head of the subject wearing the jacket 10. Additional openings 18 are cut from the jacket 10 to receive the arms of the subject. The sides of the single piece of clothlike material which may be used to form jacket 10 are attached together at 20 by conventional methods of sewing to form a closed garment having an open portion 22 for surrounding the waist of the subject. A first transverse strap 24 surrounds the thorax of the subject and is fixedly attached to the jacket 10 on its front portion by conventional sewing methods and is allowed to remain free at the back portion of the jacket to form a first loop 26 for receiving slidably therethrough the elongated strap 12 which is to be thereafter detachably connected to the bed, chair, or other supporting structure to which the subject is to be confined by means hereinafter described. A second transverse strap 28 is fixedly attached to the jacket 10 at its bottom hem by conventional methods of sewing and defines the open portion 22 for surrounding the waist of the subject. Affixedly attached by conventional sewing methods to the second transverse strap 28 is a crotch strap 30 having sufficient length to extend from the midpoint 32 of the back portion of the jacket 10 between the thighs of the subject and detachably coupling to the midpoint 34 of the front portion of the jacket 10 by detachable coupling means.

Figure 2:
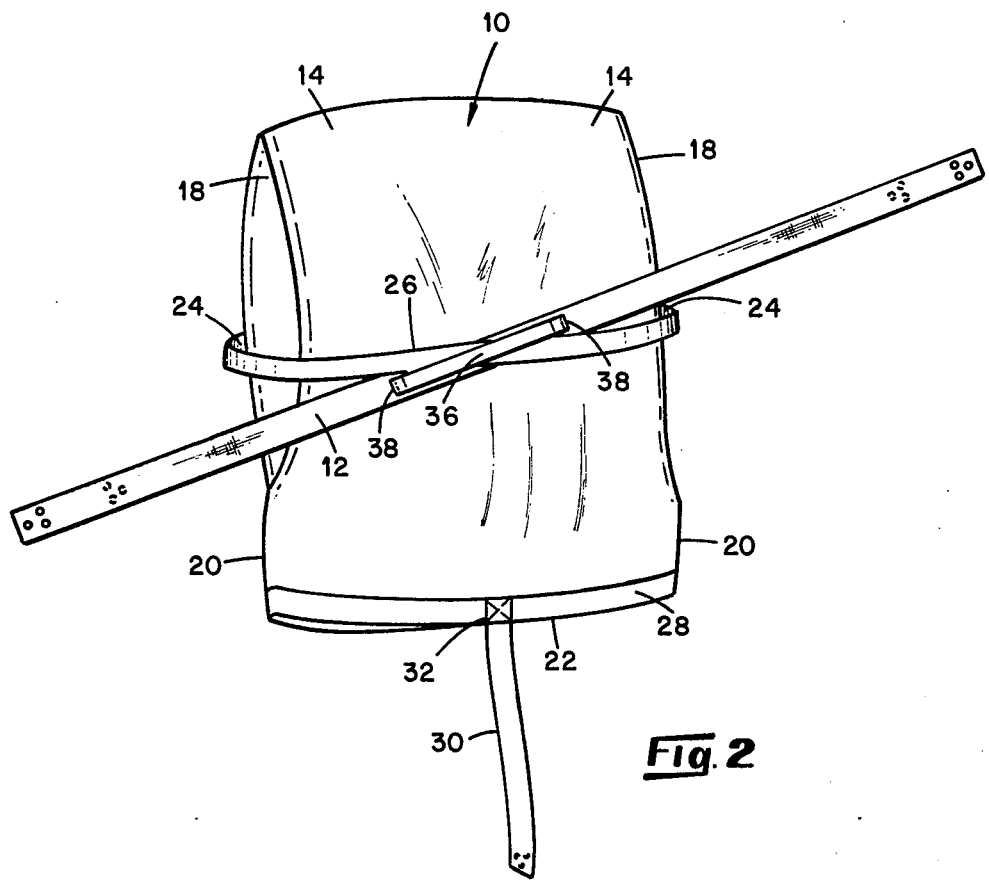
FIG. 2 is a rear perspective view showing the restraining garment of FIG. 1.

Referring to FIG. 2, the detail by which the elongated strap 12 is secured to the jacket 10 can readily be seen. The first loop 26 formed at the back of the jacket 10 slidably receives the elongated strap 12 between the loop 26 and the jacket 10 at the back of the subject. Travel of the first loop 26 along the elongated strap 12 is limited by a second loop 36, smaller than the first loop 26, and integrally attached to the elongated strap 12 on its backside by conventional sewing methods at the ends 38 of the second loop which are spatially disposed from the ends of the strap 12.

Figure 3:
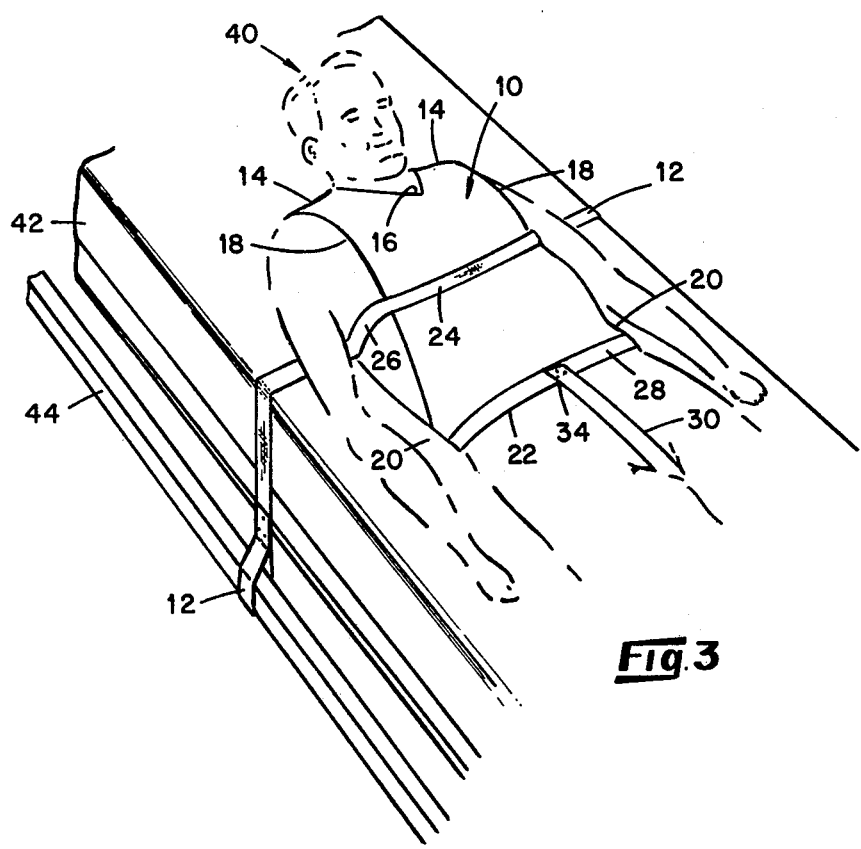
FIG. 3 is a perspective view of a patient in a hospital bed wearing the restraining garment of FIG. 1.
Figure 4:
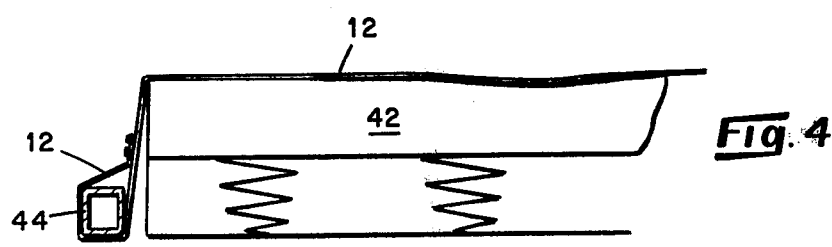
FIG. 4 is a partial cross-sectional view of a hospital bed showing the detail of one end of the restraining garment as applied.
Figure 5:
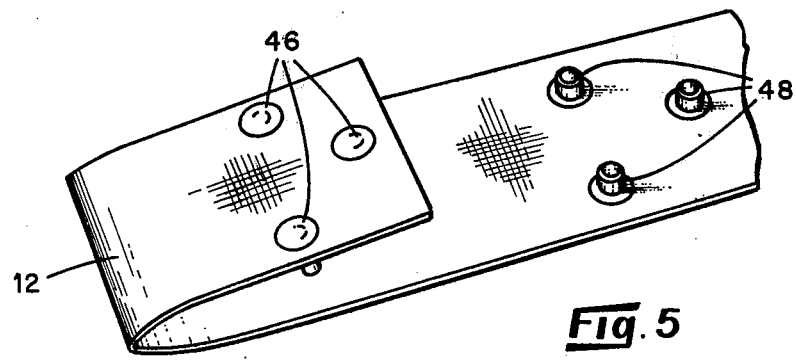
FIG. 5 is a perspective partial view on an enlarged scale of the detachable coupling means in its preferred form.

Referring to FIG. 3, the manner in which a subject 40 can be confined to a conventional hospital bed 42 is demonstrated. The jacket 10 is diposed about the upper torso of the subject 40 with its respective front and back portions snuggly and comfortably surrounding the subject. The elongated strap 12 is detachably connected to the bed frame 44 by detachable coupling means after being wrapped around the frame as illustrated in FIG. 4 and coupled as illustrated in FIG. 5. Although various forms of detachable coupling means could be utilized, the preferred embodiment uses an arrangement of triangularly spaced apart snap fasteners widely known in the industrial and automotive fields which are disengaged by pulling at the fastner in only one direction. By arranging the snap fasteners so that the proper direction of pull for disengagement lies in the center of the triangularly arranged fastners, the subject cannot escape without the assistance of someone else. Even if an aide were found, freedom could not be obtained until the proper procedure for unsnapping the fasteners was applied. This procedure consists of inserting an elongated object between the respective male and female snaps and applying a separating motion at the center of the triangularly spaced apart fasteners. This procedure will free one and sometimes two of the fastners immediately. Thereafter, the remaining engaged snaps are freed by pulling them apart in the proper direction of disengagement. FIG. 5 is a cut away view of the left end of the elongated strap 12 showing a set of male snap fastners 46 preparing to engage a set of female snap fastners 48 to complete the detachable coupling process herein described. While FIG. 5 is just a view of one of the detachable coupling means utilized on the restraining garment, it is descriptive enough to readily explain how the other detachable coupling means on the right end of the elongated strap 12 and on the crotch strap 30 operate. By detachably disconnecting the crotch strap 30, the subject 40 wearing the invention may comfortably use routine hospital facilities for relieving himself or herself without having to completely remove the garment as in prior art devices.

While the invention has been illustrated and described with respect to certain specific embodiments, it will be appreciated by those skilled in the art that many adaptions, modifications, or departures can be made within the spirit and scope of the present invention. Accordingly, it is intended by the appended claims to cover all such adaptions, modifications, or departures as are the equivalents of the herein illustrated and described restraining garment.

What is claimed is:

1. A restraining garment for comfortably confining and securing a person to a bed, chair, or other supporting structure, said device comprising:
   a. A vest member disposed around the upper torso of a subject, having interconnected front and back portions which comfortably and securely contact the respective front and back portions of the subject wearing said vest member;
   b. A first transverse strap disposed around the thorax of the subject for support and integrally attached to the front portion of the vest member for reinforcement and forming a first loop at the back portion of the vest member;
   c. A second transverse strap at the bottom hem of said vest member, disposed around the waist of the subject for support and integrally attached to the vest member for reinforcement;
   d. An elongated strap, having sufficient length to be positioned between the bed, chair, or other supporting structure and the back of the subject, having detachable coupling means at each end, said means being spatially disposed between the ends of said strap, its midpoint, and each other, so that by tightly wrapping the free ends of said strap about the frame of the bed, chair, or other supporting structure, after the said strap has been slidably received by the first loop formed at the rear of the vest member by the first transverse strap and the back portion of the vest member, and connected to said vest member by means of the first loop slidably being received by a smaller, second loop located in the center of the elongated strap and fixedly attached at both ends to the underside of the said strap, and by adjoining the coupling means located at each end of the elongated strap, the subject is confined to the approximate center of the bed, chair, or other supporting structure; and
   e. A crotch strap of sufficient length to extend between the thighs of the subject and having one end fixedly attached to the second transverse strap at the rear midpoint of the vest member, and one end detachably coupled to the second transverse strap at the front midpoint of the vest member by detachable coupling means.

2. A restraining device according to claim 1 wherein the detachable coupling means utilized on the free ends of the elongated strap and the crotch strap comprise one or more snap fastner sets of male and female interlocking snap fastners.

3. A restraining device according to claim 2 wherein the number of female snap fastners exceeds the number of male snap fastners by one or more allowing the free ends of the elongated strap and the crotch strap to be adjustable.

* * * * *